United States Patent [19]

Brabander et al.

[11] 4,168,269

[45] Sep. 18, 1979

[54] SUBSTITUTED THIENO-BENZODIAZEPINES

[75] Inventors: Herbert J. Brabander, Nanuet; Joseph W. Epstein, Monroe; Lantz S. Crawley, Spring Valley, all of N.Y.

[73] Assignee: American Cyanamid Company, Stamford, Conn.

[21] Appl. No.: 895,573

[22] Filed: Apr. 12, 1978

[51] Int. Cl.$^2$ .................. C07D 513/04; C07D 495/04
[52] U.S. Cl. ................................ 260/330.3; 424/250; 260/239.3 T
[58] Field of Search ...................... 260/329 F, 239.3 T

[56] References Cited

U.S. PATENT DOCUMENTS

| | | | |
|---|---|---|---|
| 3,951,981 | 4/1976 | Safir | 260/268 TR |
| 3,953,430 | 4/1976 | Safir | 260/239.3 T |
| 4,007,272 | 2/1977 | Safir | 424/248.51 |

OTHER PUBLICATIONS

Chem. Abstracts, vol. 86, abst. No. 29893 (1977) (Abst. of Ger. Offen., 2,552,403, pub. Aug. 12, 1976, assigned to Lilly Industries, Ltd., with Chakrabarti and Tupper as the inventors).

*Primary Examiner*—John D. Randolph
*Attorney, Agent, or Firm*—Edward A. Conroy, Jr.

[57] ABSTRACT

This disclosure describes substituted 9,10-dihydro-4H-thieno[3,4-b] [1,5]benzodiazepines which possess analgesic activity.

10 Claims, No Drawings

SUBSTITUTED THIENO-BENZODIAZEPINES

BRIEF SUMMARY OF THE INVENTION

This invention relates to new organic compounds and, more particularly, is concerned with novel substituted 9,10-dihydro-4H-thieno[3,4-b][1,5]benzodiazepines which may be represented by the following structural formula:

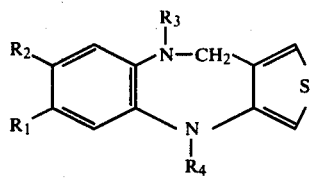

(I)

wherein $R_1$ and $R_2$ are each individually selected from the group consisting of hydrogen, chloro, hydroxy, methoxy, trifluoromethyl, nitro, amino and alkyl having up to 4 carbon atoms; $R_3$ is selected from the group consisting of hydrogen, alkyl having up to 6 carbon atoms and alkenyl having from 3 to 6 carbon atoms; and $R_4$ is selected from the group consisting of hydrogen, alkyl having up to 6 carbon atoms, cycloalkylmethyl having from 4 to 7 carbon atoms, benzyl and β-phenethyl. Suitable alkyl groups contemplated by the present invention are, for example, methyl, ethyl, isopropyl, sec-butyl, isobutyl, n-amyl, isoamyl, tert-pentyl, neopentyl, 1,2-dimethylpropyl, isohexyl, 2-methylpentyl, and the like. Suitable alkenyl groups may be, for example, allyl, methallyl, isopropenyl, 1-butenyl, crotyl, 3-butenyl, etc. Appropriate cycloalkylmethyl groups are cyclopropylmethyl, cyclobutylmethyl, cyclopentylmethyl and cyclohexylmethyl.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like but are generally insoluble in water. These compounds are organic bases and thus are capable of forming acid-addition and quaternary ammonium salts with a variety of organic and inorganic salt-forming reagents. Thus, acid-addition salts, formed by admixture of the organic free base with up to three equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. In like manner, quaternary ammonium salts may be formed by reaction of the free bases with a variety of organic esters of sulfuric, hydrohalic and aromatic sulfonic acids. The organic reagents employed for quaternary ammonium salt formation are preferably lower alkyl halides. However, other organic reagents are suitable for quaternary ammonium salt formation and may be selected from among a diverse class of compounds including benzyl chloride, phenethyl chloride, naphthyl-methyl bromide, dimethyl sulfate, methyl benzenesulfonate, ethyl toluenesulfonate, allyl chloride, methallyl bromide and crotyl bromide. The acid-addition and quaternary ammonium salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition and quaternary ammonium salts.

Certain of the novel compounds of the present invention may be readily prepared as set forth in the following reaction scheme:

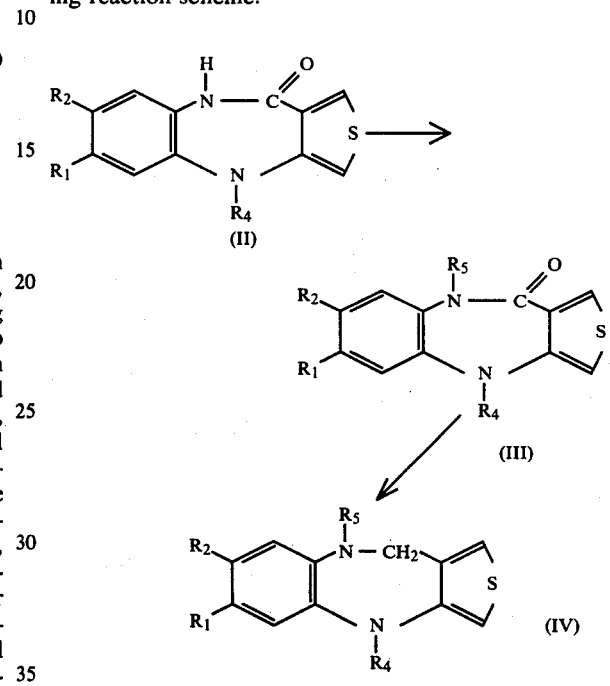

wherein $R_5$ is alkyl having up to 6 carbon atoms or alkenyl having from 3 to 6 carbon atoms and $R_1$, $R_2$ and $R_4$ are as hereinabove defined. Alkylation at the 9-position of the 4,9-dihydro-10H-(thieno)[3,4-b][1,5]benzodiazepin-10-one (II) is accomplished by first treating (II) with 50% sodium hydride in mineral oil in dimethylformamide as solvent for a few hours at ambient temperatures. Then, an alkyl or alkenyl halide of the formula: $R_5$-X wherein X is chloro, bromo or iodo is added and the reaction mixture is stirred at ambient temperatures for a period of time of 8–12 hours to provide the 9-substituted derivative (III). Reduction of the 9-substituted derivative (III) to the final product (IV) is achieved with either lithium aluminum hydride or 1 M borane in tetrahydrofuran as solvent at the reflux temperature for a period of time of 12–24 hours.

Other novel compounds of the present invention may be prepared as set forth in the following reaction scheme:

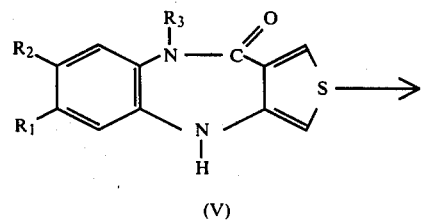

(V)

-continued

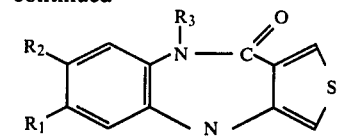

(VI)

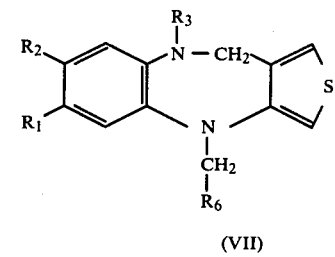

(VII)

wherein $R_6$ is alkyl having up to 5 carbon atoms, cycloalkyl having from 3 to 6 carbon atoms, phenyl or benzyl; and $R_1$, $R_2$, and $R_3$ are as hereinabove defined. Acylation at the 4-position of the 4,9-dihydro-10H-thieno[3,4-b][1,5]-benzodiazepin-10-one (V) is accomplished by treating (V) with an acyl halide of the formula: $R_6$-CO-X wherein X is chloro or bromo. This acylation is best performed in an inert solvent such as benzene, toluene, or dioxane at the reflux temperature for a period of time of 2-6 hours and preferably in the presence of an acid acceptor such as triethylamine or soda ash. Reduction of the 4-acyl-4,9-dihydro-10H-thieno[3,4-b][1,5]benzodiazepin-10-one (VI) then provides the corresponding 9,10-dihydro-4-substituted-4H-thieno[3,4-b][1,5]-benzodiazepine (VII). A variety of chemical reducing agents may be used in this reduction including sodium sulfide, sodium borohydride, sodium dithionite and lithium aluminum hydride. The reduction may also be carried our with active metals such as zinc, tin or iron in acetic acid of mineral acids such as hydrochloric acid. Reduction with metal couples such as the copper-zinc couple, the tin-mercury couple, aluminum amalgam, soidum amalgam or magnesium amalgam; and reduction with formic acid may also be used. However, reduction with borane under a nitrogen atmosphere in tetrahydrofuran as solvent is the preferred procedure. The borane is added as a one molar solution at ice-bath temperature over a period of 10-15 minutes followed by refluxing for 8-12 hours. When aqueous systems are used in the aforementioned chemical reductions, it is at times desirable to utilize a water-miscible organic solvent, particularly when the starting compound is of limited solubility in the reaction mixture. The water-miscible solvent does not alter the course of the reduction but merely provides for more efficient reduction, e.g. a shorter reaction time by providing more intimate contact of the reagents. A large number of such solvents are available for this purpose and include, among others, dimethylformamide, dimethoxyoxyethane, methanol, ethanol, dioxane, tetrahydrofuran, and the like.

The compounds of this invention are active analgesic agents when measured by the "writhing syndrome" test for analgesic activity as described by Siegmund, et al., Proc. Soc. Exp. Biol. and Med., 95, 729 (1957), with modifications. This method is based upon the reduction of the number of writhes following the intraperitoneal injection of one mg./kg. of body weight of phenyl-p-quinone in male Swiss albino mice weighing 18-25 g. The syndrome is characterized by intermittent contractions of the abdomen, twisting and turning of the trunk and extension of the hind legs, beginning 3 to 5 minutes after injection of the phenyl-p-quinone. The test compounds are administered orally at the indicated dose to groups of 2 mice each, 30 minutes before injection of the phenyl-p-quinone. The total number of writhes exhibited by each group of mice is recorded for a 3 minute period commencing 15 minutes after injection of the phenyl-p-quinone. A compound is considered active if it reduces the total number of writhes in 2 test mice from a control value of approximately 30 per pair to a value of 18 or less. Table I summarizes the results of this test on representative compounds of this invention.

TABLE I

| Compound | Dose mg./kg. | Result |
|---|---|---|
| 9,10-Dihydro-9-methyl-4H-thieno-[3,4-b] [1,5]benzodiazepine | 100 | Active |
|  | 50 | Active |
| 9,10-Dihydro-4H-thieno[3,4-b]-[1,5]benzodiazepine | 50 | Active |
| Aspirin | 200 | Active |
|  | 75 | Active |
|  | 50 | Active |
| Acetominophen | 200 | Active |
|  | 100 | Active |
|  | 50 | Active |
| Controls |  | 30 |

The compounds of this invention also exhibit analgesia in warm-blooded animals when measured by the Brewers' Yeast Pressure Pain Test. To determine analgesic activity, a modification of the method of Randall and Selitto [Arch. Int. Pharmacodyn, 111, 409, (1957)] is used. This test measures the pain threshold of rats whose paws are made sensitive to pressure by the injection of 0.1 ml. of a 20% aqueous suspension of brewers' yeast into the plantar surface of the left hind paw. Constantly increasing force at the rate of 16 g./sec. is applied to the swollen paw using an Analgesy Meter, Ugo Basile. The pressure is cut off at 250 g. of force when there is no response (sudden struggle or vocalization). Control rats, treated with only starch vehicle, respond to a pressure or force of about 30 g. Pressure-pain thresholds are always recorded 2 hours after brewers' yeast administration. The test compounds are administered orally at the same time as the yeast at the indicated dose. Ratios of treated (T)/control (C) reaction thresholds are calculated as estimates of analgesic efficacy (degree of analgesia obtainable). Test compounds are considered active if they produce a 100% elevation of pain threshold (T/C 1.37). The results of this test on representative compounds of this invention appear in Table II.

TABLE II

| Compound | Dose mg./kg. | Result |
|---|---|---|
| 9,10-Dihydro-9-methyl-4H-thieno-[3,4-b] [1,5]benzodiazepine | 60 | Active |
| 9,10-Dihydro-4H-thieno[3,4-b]-[1,5]benzodiazepine | 90 | Active |
| Aspirin | 100 | Active |
|  | 200 | Active |
| Acetominophen | 100 | Active |
|  | 200 | Active |

TABLE II-continued

| Compound | Dose mg./kg. | Result |
|---|---|---|
| Controls | | 1.0 |

The compounds of this invention exhibit analgesic activity when measured by a modification of the method of D. C. Atkinson and A. Cowan, J. Pharm. Pharmac., 26, 727 (1974). In this test, male albino Wistar strain rats from Royalhart farms, weighing 120-150 g. are deprived of food for about 20 hours. A 40% suspension of brewers' yeast in physiological saline is injected at a concentration of 0.25 ml./rat into the plantar surface of the left hind paw of each rat. Three hours later, at which time an inflammation of the injected paw has developed, a pre-drug assessment of walking gait is made for each rat according to the following scoring system:

- 0 = Normal gait in the presence of a severely inflamed paw. There is continuous use of the foot pad.
- 0.5 = As above with intermittent mild limping.
- 1.0 = Constant limping, but continuous use of the foot pad.
- 1.5 = Limping with occasional three-legged gait (paw kept off walking surface) or intermittent use of digits in combination with foot pad.
- 2.0 = Continuous three-legged gait and/or only the tips of the digits touch the walking surface. There is no use of the foot pad.

More than 95% of the rats exhibit a gait score of 2 before given a test compound. Test compounds are administered orally, by gavage, in a suitable vehicle at a volume of 0.5 ml./100 g. of body weight. One and/or 2 hours later a post-drug assessment of walking gait is made as described above. The criterion of an analgesic response for each rat is a 50% reversal of the abnormal gait score (post-drug) from the pre-drug score. The results of this test on representative compounds of the present invention appear in Table III.

TABLE III

| Compound | Result |
|---|---|
| 9,10-Dihydro-9-methyl-4H-thieno[3,4-b][1,5]benzodiazepine | Active |
| 9,10-Dihydro-4H-thieno[3,4-b][1,5]benzodiazepine | Active |
| 9,10-Dihydro-4-methyl-4H-thieno[3,4-b][1,5]benzodiazepine | Active |
| 9,10-Dihydro-9-ethyl-4H-thieno[3,4-b][1,5]benzodiazepine hydrochloride | Active |
| 9,10-Dihydro-4-ethyl-4H-thieno[3,4-b][1,5]benzodiazepine | Active |
| 6,7-Dichloro-9,10-dihydro-9-methyl-4H-thieno[3,4-b][1,5]benzodiazepine | Active |
| Aspirin | Active |
| Acetaminophen | Active |

The compounds of this invention also show antipyretic activity by their ability to reduce a hyperthermic response in warm-blooded animals, induced by the subcutaneous injection of a suspension of brewers' yeast. This is a modification of the method of Teotino, et al., J. Med. Chem., 6, 248 (1963). A 40% suspension of brewers' yeast in distilled water is administered to groups of 5 to 19 rats subcutaneously at 1.0 ml./100 g. of body weight. Eighteen hours later, rectal temperatures are recorded and test compounds in 2% starch vehicle at the indicated dose or vehicle alone is administered. Rectal temperatures are recorded 4 hours later and the results are compared with the starch vehicle controls and with reference anti-pyretic agents. The results of representative compounds of this invention with regard to the amount of temperature reduction they induce is recorded in Table IV.

TABLE IV

| Compound | Dose mg./kg. | Temperature Reduction °F. |
|---|---|---|
| 9,10-Dihydro-9-methyl-4H-thieno[3,4-b][1,5]benzodiazepine | 50 | −1.9 |
|  | 25 | −1.8 |
| 9,10-Dihydro-4H-thieno[3,4-b][1,5]benzodiazepine | 200 | −1.7 |
| 9,10-Dihydro-4-methyl-4H-thieno[3,4-b][1,5]benzodiazepine | 200 | −0.9 |
|  | 100 | −1.3 |
| 9,10-Dihydro-9-ethyl-4H-thieno[3,4-b][1,5]benzodiazepine hydrochloride | 200 | −1.3 |
| 9,10-Dihydro-4-ethyl-4H-thieno[3,4-b][1,5]benzodiazepine | 200 | −2.4 |
|  | 100 | −1.8 |
| 6,7-Dichloro-9,10-dihydro-9-methyl-4H-thieno[3,4-b][1,5]benzodiazepine | 100 | −2.1 |
| 9,10-Dihydro-6,7,9-trimethyl-4H-thieno[3,4-b][1,5]benzodiazepine | 200 | −0.6 |
| 9,10-Dihydro-4-ethyl-9-methyl-4H-thieno[3,4-b][1,5]benzodiazepine | 100 | −1.6 |
| Aspirin | 100 | −2.6 |
| Acetaminophen | 100 | −3.3 |
| Controls |  | +0.9 |

The active compounds of this invention can be used in compositions such as tablets; the principal active ingredient is mixed with conventional tabletting ingredients such as corn starch, lactose, sucrose, sorbitol, talc, stearic acid, magnesium stearate, dicalcium phosphate, gums, or similar materials such as non-toxic, pharmaceutically acceptable diluents or carriers. These tablets or pills can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or be delayed in release. A variety of materials can be used for such enteric layers or coatings, such materials including a number of polymeric acids of mixtures of polymeric acids with such materials as shellac, shellac and cetyl alcohol, cellulose and the like. A particularly advantageous enteric coating comprises a styrene maleic acid copolymer together with known materials contributing to the enteric properties of the coating.

The liquid forms in which the novel compounds of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary doses for warm-blooded animal subjects, each unit containing a predetermined quantity of active component calculated to product the desired therapeutic effect in association with a pharmaceutical diluent, carrier or vehicle.

The specification for the dosage forms of the novel compounds of this invention are indicated by characteristics of the active component and the particular therapeutic effect desired or the limitations inherent in the art of compounding such an active component.

Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The following examples described the preparation of representative compounds of this invention.

EXAMPLE 1

9,10-Dihydro-9-methyl-4H-thieno[3,4-b][1,5]benzodiazepine

A mixture of 3.5 g. of 4,9-dihydro-9-methyl-10H-thieno[3,4][1,5]benzodiazepin-10-one [U.S. Pat. No. 3,953,430 (Example 26)] in 60 ml. of dry tetrahydrofuran is stirred under nitrogen. While stirring, 45 ml. of 1 M borane in tetrahydrofuran is added dropwise. When addition is complete the mixture is heated under reflux for 3 hours. The reaction mixture is cooled and 13 ml. of 6 N hydrochloric acid is added with stirring. The tetrahydrofuran is distilled off at atmospheric pressure. The reaction mixture is cooled in an ice bath and swirled with 10 g. of sodium hydroxide pellets. The mixture is extracted twice with benzene. The benzene extracts are washed with water, dried over sodium sulfate, filtered and concentrated to a viscous brown oil. This oil is triturated with 100 ml. of hexane:ether and the solvents are removed giving a dark brownish green oil. This oil is purified by conventional chromatographic techniques using an alumina column and 40% methylene chloride 60% hexane. Concentration of the solvent mixture yields a gray-blue crystalline product. The crystals are dissolved in boiling hexane, cooled and then collected, washed with hexane and dried to give the final desired product, mp. 110°–112° C.

EXAMPLE 2

9,10-Dihydro-4H-thieno[3,4-b][1,5]benzodiazepine

A reaction mixture comprising 3.8 g. of lithium aluminum hydride in 100 ml. of dry tetrahydrofuran, 5 g. of 4,9-dihydro-10H-thieno[3,4-b][1,5]benzodiazepin-10-one [U.S. Pat. No. 3,953,430 (Example 25)] and 125 ml. of dry tetrahydrofuran is heated, with stirring under reflux for 18 hours. The reaction mixture is cooled and 4 ml. of water is carefully added dropwise with stirring and ice bath cooling. Following this, 4 ml. of 15% sodium hydroxide and 12 ml. of water are added. The mixture is filtered and the precipitate is washed thoroughly with tetrahydrofuran and ether. The combined organic phases are dried over sodium sulfate filtered and the filtrate is concentrated to dryness. The dark brownish-green crystals are triturated in hexane, filtered, washed with hexane and dried. The product is heated to boiling in 50 ml. of chloroform, filtered and the filtrate is combined with 50 ml. of hexane and cooled in a chill room. The crystals are recovered by filtration, washed with hexane and dried. Recrystallization from chloroform-hexane is repeated. A 200 mg. portion of these crystals is recrystallized by dissolving in 10 ml. of chloroform with warming, treating with activated charcoal, filtering through diatomaceous earth and adding 20 ml. of hexane to the filtrate. These crystals are collected, washed with hexane, and dried giving the desired final product, mp. 167°–169° C.

EXAMPLE 3

4,9-Dihydro-4-phenylacetyl-10H-thieno[3,4-b][1,5]benzodiazepin-10-one

A reaction mixture comprising 6.48 g. of 4,9-dihydro-10H-thieno[3,4-b][1,5]benzodiazepin-10-one and 25 g. of phenylacetyl chloride in 100 ml. of benzene is refluxed with stirring for 3 hours. The mixture is evaporated to an amber oil, combined with 100 ml. of ethanol and 6 ml. of 5 N sodium hydroxide and allowed to stand at room temperature for one hour. This solution is evaporated to an oily residue which is triturated with water and filtered, giving the desired product as pale pink crystals, mp. 165°–168° C.

EXAMPLE 4

9,10-Dihydro-4-phenethyl-4H-thieno[3,4-b][1,5]benzodiazepine hydrochloride

A 6.12 g. portion of 4,9-dihydro-4-phenylacetyl-10H-thieno[3,4-b][1,5]benzodiazepin-10-one is suspended in 100 ml. of tetrahydrofuran under argon and stirred with cooling in an ice bath. To this is added 90 ml. of 1 M diborane in tetrahydrofuran over a period of 10 minutes. The mixture is then stirred at room temperature until solution is complete, refluxed for 18 hours, cooled and 45 ml. of 6 N hydrochloric acid is added. The tetrahydrofuran is removed in vacuo and 75 ml. of 5 N sodium hydroxide is added giving the desired final product, mp. 195°–197° C.

EXAMPLE 5

4-Cyclopropylcarbonyl-4,9-dihydro-10H-thieno[3,4-b][1,5]benzodiazepin-10-one

To a mixture of 10.0 g. of 4,9-dihydro-10H-thieno[3,4-b][1,5]benzodiazepin-10-one in 100 ml. of benzene is added 11 g. of cyclopropanecarbonyl chloride. The mixture is refluxed for 3 hours and then filtered. The filtrate is washed four times with aqueous sodium bicarbonate, the organic layer is dried over magnesium sulfate and then is filtered. The filtrate is evaporated to give the desired product as pale pink crystals, mp. 245°–247° C.

EXAMPLE 6

4-Cyclopropylcarbonyl-9,10-dihydro-4H-thieno[3,4-b][1,5]benzodiazepine hydrochloride To 5.69 g. of 4-cyclopropylcarbonyl-4,9-dihydro-10H-thieno[3,4-b][1,5]benzodiazepin-10-one in 100 ml. of tetrahydrofuran is added 120 ml. of 1 M borane in tetrahydrofuran under argon, with stirring in an ice bath. The mixture is refluxed for 18 hours, then chilled and 60 ml. of 6 N hydrochloric acid is cautiously added. Most of the solvent is evaporated and 100 ml. of 5 N sodium hydroxide is added. The mixture is extracted with methylene chloride, dried over magnesium sulfate and evaporated giving a gum. Excess hydrochloric acid and ethanol are added to the gum and then evaporated giving a second gum. Ethanol is added to this second gum producing crystals which are recovered giving the desired product as colorless crystals, mp. 157°–159° C. (dec.).

EXAMPLE 7

9,10-Dihydro-4-methyl-4H-thieno[3,4-b][1,5]benzodiazepine

A mixture comprising 4 g. of 4,9-dihydro-4-methyl-10H-thieno[3,4-b][1,5]benzodiazepin-10-one [U.S. Pat. No. 3,953,430 (Example 2)] in 75 ml. of tetrahydrofuran is combined with 2 g. of lithium aluminum hydride in 50 ml. of tetrahydrofuran and refluxed under nitrogen with stirring for 10 hours. A 2 ml. portion of water is carefully added dropwise with cooling followed by 2 ml. of 15% sodium hydroxide and 6 ml. of water. The mixture is filtered and the precipitate is washed thoroughly with ether. The filtrate and washings are combined, dried over sodium sulfate, filtered and concentrated to a semicrystalline brown oil. The product is triturated with hexane producing a tan crystalline solid. This solid is recovered, washed thoroughly with hexane and dried. This crystalline material is purified by column chromatography (alumina activity II), eluting with methylene chloride:hexane (50:50). Evaporation of the solvents yields a solid which is triturated with hexane and washed with ether, giving the desired product as pale blue crystals, mp. 125°–127° C.

EXAMPLE 8

4,9-Dihydro-9-methyl-4-phenylacetyl-10H-thieno[3,4-b][1,5]benzodiazepin-10-one

A slurry of 6.90 g. of 4,9-dihydro-9-methyl-10H-thieno[3,4-b][1,5]benzodiazepin-10-one and 4.36 ml. (5.10 g.) of phenylacetyl chloride in 100 ml. of benzene is refluxed with stirring for 5 hours. The reaction mixture is filtered while hot through diatomaceous earth. The filtrate is washed twice with aqueous sodium bicarbonate and dried over magnesium sulfate causing crystals to form. The drying agent and crystals are washed with chloroform and then chloroform:methanol (9:1). The washings are evaporated to residual crystals which are combined twice with ethanol and filtered giving the desired product as tan crystals, mp. 210°–212° C.

EXAMPLE 9

9,10-Dihydro-9-methyl-4-phenethyl-4H-thieno[3,4-b][1,5]benzodiazepine

To a slurry of 6.0 g. of 4,9-dihydro-9-methyl-4-phenylacetyl-10H-thieno[3,4-b][1,5]benzodiazepin-10-one in 100 ml. of dried tetrahydrofuran, cooled in an ice bath, is added 125 ml. of 1 M borane in tetrahydrofuran, dropwise over 10 minutes. The mixture is stirred at room temperature for one hour, refluxed for 6 hours and then stirred at room temperature for 16 hours. The reaction is decomposed by the addition of 50 ml. of 6 N hydrochloric acid and then 75 ml. of 5 N sodium hydroxide is added. Most of the solvent is evaporated, the residue is extracted with methylene chloride and the extract is evaporated to an oil. This oil is dissolved in hot hexane, filtered through diatomaceous earth and evaporated to an oil which crystallizes giving the desired product as colorless crystals, mp. 53°–56° C.

EXAMPLE 10

4,9-Dihydro-9-ethyl-10H-thieno[3,4-b][1,5]benzodiazepin-10-one

An 11.8 g. portion of 4,9-dihydro-10H-thieno[3,4-b][1,5]benzodiazepin-10-one is reacted with 2.8 g. of 50% sodium hydride in mineral oil in 175 ml. of dimethylformamide. After 2 hours 11.5 g. of ethyl iodide is added and the mixture is stirred overnight at room temperature. The reaction mixture is poured into ice-water. After 3 hours the brown crystals are collected, washed with water and then ether and dried. The solid is heated to boiling in 75 ml. of methanol, filtered and the filtrate is treated with charcoal, reheated to the boil and filtered through diatomaceous earth. To the filtrate is added, portionwise with swirling, 100 ml. of water. The mixture is cooled in a chill room and the solid is collected, washed with ether and dried giving the desired product, mp. 175°–177° C.

EXAMPLE 11

9,10-Dihydro-9-ethyl-4H-thieno[3,4-b][1,5]benzodiazepine hydrochloride

A mixture of a 4.0 g. portion of 4,9-dihydro-9-ethyl-10H-thieno[3,4-b][1,5]benzodiazepin-10-one in 100 ml. of dried tetrahydrofuran and 5.2 g. of lithium aluminum hydride in 135 ml. of tetrahydrofuran is refluxed overnight. The reaction mixture is cooled in an ice bath and 5 ml. of water is carefully added dropwise with stirring. Then 5 ml. of 15% sodium hydroxide followed by 15 ml. of water are added to the stirring mixture. The complex is filtered and washed repeatedly with ether. The combined filtrate and washings are dried over sodium sulfate, filtered and concentrated to a dark green oil. The oil is purified by conventional chromatographic techniques using an alumina column and 40% methylene chloride in hexane. Concentration of the solvent mixture yields a dark green oil which is combined with hexane and diethyl ether and stored in a chill room for 48 hours. The solvents are removed and the residue is boiled five times with 50 ml. portions of hexane. The hexane extracts are treated with charcoal, filtered through diatomaceous earth, and concentrated to a green oil. The oil is dissolved in 50 ml. of ether and 7 ml. of 3 N ethanolic hydrochloric acid is added. The crystals are collected, washed with ether and recrystallized twice from hot ethanol with cooling to give the desired product as the hydrochloride salt, mp. 201°–203° C.

EXAMPLE 12

4-Acetyl-4,9-dihydro-10H-thieno[3,4-b][1,5]benzodiazepin-10-one

A reaction mixture comprising 9.9 g. of 4,9-dihydro-10H-thieno[3,4-b][1,5]benzodiazepin-10-one and 4 g. (3.7 ml.) of acetyl chloride in 100 ml. of benzene is refluxed for 3 hours and then allowed to stand at room temperature overnight. The precipitate is collected, washed with benzene and dried. The solid is crystallized twice from hot methanol with cooling giving the desired product, mp. 228°–230° C.

EXAMPLE 13

9,10-Dihydro-4-ethyl-4H-thieno[3,4-b][1,5]benzodiazepine

A reaction mixture comprising 5 g. of 4-acetyl-4,9-dihydro-10H-thieno[3,4-b][1,5]benzodiazepin-10-one in 225 ml. of dried tetrahydrofuran and 6.4 g. of lithium aluminum hydride in 150 ml. of dried tetrahydrofuran under nitrogen is stirred with heating to reflux overnight. A 6.5 ml. portion of water is added cautiously with stirring and cooling followed by 6.5 ml. of 15% sodium hydroxide and 19 ml. of water. The complex is filtered and washed thoroughly with ether. The combined filtrate and washings is dried over sodium sulfate and concentrated to a dark brown viscous oil. The oil is crystallized by treatment with 50 ml. of ether:hexane (50:50). The crystalline product is dissolved in 15 ml. of 40% methylene chloride in hexane and chromatographed on an alumina column eluting with 40% methylene chloride in hexane. Fractions 2–8 (50 ml. each) are combined and concentrated giving olive green crystals. These crystals are triturated in hexane, washed with hexane and dried giving the desired product, mp. 85°–87° C.

EXAMPLE 14

4,9-Dihydro-9-hexyl-10H-thieno[3,4-b][1,5]benzodiazepin-10-one

An 11.8 g. portion of 4,9-dihydro-10H-thieno[3,4-b][1,5]benzodiazepin-10-one is combined with 2.8 g. of 50% sodium hydride in mineral oil and 175 ml. of dimethylformamide and stirred for 2 hours. A 15.7 g. (11 ml.) portion of n-hexyl iodide is added and the mixture is stirred overnight. The reaction mixture is poured into ice water and the brown oil is separated and dissolved in methylene chloride. The dimethylformamide-water mixture is extracted twice with methylene chloride. All methylene chloride portions are combined, washed with water, dried over sodium sulfate, filtered and concentrated to a dark brown oil. This oil is dissolved in 10 ml. of methylene chloride and chromatographed on an alumina column. The column is eluted with 500 ml. of hexane followed by 30% methylene chloride in hexane for fractions 5–13 and methylene chloride:hexane (50:50) for fractions 14–19. Fraction 6 is concentrated to a dark brown viscous oil (A). Fractions 7–19 are combined and concentrated to dryness (B). (A) and (B) both crystallize in hexane and are combined, filtered, washed with hexane and dried. The product is dissolved with warming in 50 ml. of benzene and filtered. To the filtrate is added 100 ml. of hexane and the mixture is cooled overnight. The solid is collected, washed with ether and dried, giving the desired product, mp. 100°–102° C.

EXAMPLE 15

9,10-Dihydro-9-hexyl-4H-thieno[3,4-b][1,5]benzodiazepine hydrochloride

A solution of 7.8 g. of 4,9-dihydro-9-hexyl-10H-thieno[3,4-b][1,5]benzodiazepin-10-one in 100 ml. of dried tetrahydrofuran is added dropwise, with stirring, under nitrogen, to a suspension of 4.2 g. of lithium aluminum hydride in 135 ml. of tetrahydrofuran. The reaction mixture is then heated under reflux with stirring for 20 hours. The mixture is cooled in an ice bath and stirred under nitrogen while 4 ml. of water, 4 ml. of 15% sodium hydroxide and then 12 ml. of water are added. The complex is filtered and washed thoroughly with ether. The combined filtrate and washings are dried over sodium sulfate and filtered. The solvents are removed and the residue is triturated with hexane. The blue-green oil is dissolved in 50 ml. of ether and treated with 10 ml. of 3 N ethanolic hydrochloric acid followed by an additional 150 ml. of ether and stored in a chill room producing a purple syrup. The solvent mixture is concentrated to a residue. The residue is dissolved with warming in 25 ml. of ethanol, added to the purple syrup and warmed to solution. A 25 ml. portion of ether is added, the mixture is stored in a chill room and the crystals are recovered, washed with 25 ml. of ether and dried (crop #1). A second crop is recovered from the rechilled mother liquor in the same manner. Both crops are combined, heated to solution in 20 ml. of ethanol, filtered and the filtrate is diluted with 100 ml. of ether. Cooling produces crystals which are collected, washed with ether and dried giving the desired product, mp. 147°–149° C.

EXAMPLE 16

6,7-Dimethyl-1,3,4,9-tetrahydro-10H-thieno[3,4-b][1,5]benzodiazepin-10-one

A 34 g. portion of 4,5-dimethyl-O-phenylenediamine in one liter of toluene is refluxed with stirring. After 70 minutes, 40 g. of tetrahydro-4-oxo-3-thiophene carboxylic acid, methyl ester in 500 ml. of toluene is added. Refluxing is continued for an additional 4.5 hours and then the mixture is allowed to stand overnight. The mixture is cooled and the precipitate is collected and dried giving 50.25 g. of 6,7-dimethyl-1,3,4,9-tetrahydro-10H-thieno[3,4-b][1,5]benzodiazepin-10-one.

Employing the same general procedure, the following starting materials produce the corresponding mixture of products:

| Starting Material | Products |
| --- | --- |
| 4-methoxy-o-phenylenediamine | 7-methoxy-and 6-methoxy-1,3,4,9-tetrahydro-10H-thieno-[3,4-b] [1,5]benzodiazepin--10-one |
| 4-hydroxy-o-phenylenediamine | 7-hydroxy-and 6-hydroxy-1,3,4,9-tetrahydro-10H-thieno-[3,4-b] [1,5]benzodiazepin--10-one |
| 4-trifluoromethyl-o-phenylenediamine | 7-trifluoromethyl- and 6--trifluoromethyl-1,3,4,9--tetrahydro-10H-thieno[3,4--b] [1,5]benzodiazepin-10--one |

EXAMPLE 17

4,9-Dihydro-6,7-dimethyl-10H-thieno[3,4-b][1,5]benzodiazepin-10-one

To a slurry of 18.8 g. of 6,7-dimethyl-1,3,4,9-tetrahydro-10H-thieno[3,4-b][1,5]benzodiazepin-10-one in 150 ml. of pyridine, stirred in an ice bath, is added 10.1 g. of N-chlorosuccinimide portionwise over 15 minutes. The mixture is heated on a steam bath for 30 minutes, poured into one liter of water and allowed to stand overnight. The solid is filtered, washed with water, 1 N hydrochloric acid, three times with water and diethyl ether and dried giving the desired final product, mp. 233°–238° C. (dec.).

Employing the same general procedure the following starting materials produce the corresponding mixture of products:

| Starting Materials | Products |
| --- | --- |
| 7-methoxy and 6-methoxy-1,3,4,9--tetrahydro-10H-thieno[3,4-b]-4,9-dihydro-10H-thieno-[1,5]benzodiazepin-10-one | 7-methoxy- and 6-methoxy-[3,4-b] [1,5]benzodiazepin--10-one |
| 7-hydroxy and 6-hydroxy-1,3,4,9--tetrahydro-10H-thieno[3,4-b]-[1,5]benzodiazepin-10-one | 7-hydroxy- and 6-hydroxy--4,9-dihydro-10H-thieno-[3,4-b] [1,5]benzodiazepin--10-one |
| 7-trifluoromethyl and 6-trifluoromethyl-1,3,4,9-tetrahydro-10H--trifluoromethyl-4,9-di--thieno[3,4-b] [1,5]benzodiaze- | 7-trifluoromethyl- and 6-hydro-10H-thieno[3,4-b]- |

| -continued | |
|---|---|
| Starting Materials | Products |
| pin-10-one | [1,5]benzodiazepin-10-one |

EXAMPLE 18

9,10-Dihydro-6,7,9-trimethyl-4H-thieno[3,4-b][1,5]benzodiazepine

To a slurry of 3.88 g. of 4,9-dihydro-6,7,9-trimethyl-10H-thieno[3,4-b][1,5]benzodiazepin-10-one in 100 ml. of tetrahydrofuran, cooled in an ice bath and stirred under argon is added 60 ml. of 1 M borane in tetrahydrofuran, dropwise over 15 minutes. The mixture is stirred for one hour at room temperature, refluxed for 18 hours, cooled in an ice bath and decomposed by the addition of 30 ml. of 6 N hydrochloric acid. The mixture is stirred for one hour, 30 ml. of 10 N sodium hydroxide is added, stirring is continued for one hour and the tetrahydrofuran is evaporated. The remaining aqueous layer is filtered giving blue tinted crystals. These crystals are combined with 125 ml. of absolute methanol and saturated with gaseous hydrogen chloride. A 25 ml. portion of water is added and the mixture is heated on a steam bath until solution is complete. The methanol is evaporated in vacuo, 150 ml. of water is added and the solution is made basic with 10 N sodium hydroxide. The solution is extracted with methylene chloride and the extract is dried over magnesium sulfate and evaporated giving the desired product as blue crystals, mp. 121°–125° C.

Employing the same general procedure, the following starting materials produce the corresponding mixture of products:

| Starting Materials | Products |
|---|---|
| 7-methoxy and 6-methoxy-4,9-dihydro--10H-thieno[3,4-b] [1,5]benzodiazepin-10-one | 9,10-dihydro-7-methoxy- and 6-methoxy-4H-thieno[3,4-b] [1,5]benzodiazepine |
| 7-hydroxy and 6-hydroxy-4,9-dihydro--10H-thieno[3,4-b] [1,5]benzodiazepin-10-one | 9,10-dihydro-7-hydroxy- and 6-hydroxy-4H-thieno[3,4-b] [1,5]benzodiazepine |
| 7-trifluoromethyl and 6-trifluoromethyl-4,9-dihydro-10H-thieno[3,4-b]-[1,5]benzodiazepin-10-one | 9,10-dihydro-7-trifluoromethyl- and 6-trifluoromethyl-4H-thieno[3,4-b]-[1,5]benzodiazepine |

EXAMPLE 19

7-Amino-4,9-dihydro-10H-thieno[3,4-b][1,5]benzodiazepin-10-one

A 7.8 g. portion of 4,9-dihydro-7-nitro-10H-thieno[3,4-b][1,5]benzodiazepin-10-one in a mixture of 200 ml. of pyridine and 50 ml. of methanol with 200 mg. of 10% palladium on carbon catalyst was shaken for 2 hours in a Parr hydrogenator. The catalyst was filtered and the solvents were removed under vacuum on the steam bath. The residue was dissolved in dilute hydrochloric acid, filtered, and the filtrate was made alkaline with sodium hydroxide. The crystals which form are recovered by filtration and air dried given the desired product as a brown powder, m.p. 212°–215° C.

EXAMPLE 20

4,9-Dihydro-9-propyl-10H-thieno[3,4-b][1,5]benzodiazepin-10-one

An 11.8 g. portion of 4,9-dihydro-10H-thieno[3,4-b][1,5]benzodiazepin-10-one and 2.8 g. of 50% sodium hydride in mineral oil in 175 ml. of dimethylformamide is stirred for 2 hours. A 12.6 g. portion of n-propyl iodide is added and the mixture is stirred overnight at room temperature. The reaction mixture is poured into ice water. After 3 hours the brown crystals are recovered by filtration, washed thoroughly with water, then ether and dried. This solid is heated to boiling in 75 ml. of methanol, filtered while hot and the filtrate is stored in a chill room. The crystals which form are recovered by filtration, washed with ether and dried giving the desired product, mp. 166°–167° C.

EXAMPLE 21

9,10-Dihydro-9-propyl-4H-thieno[3,4-b][1,5]benzodiazepine

A 5 g. portion of 4,9-dihydro-9-propyl-10H-thieno[3,4-b][1,5]benzodiazepin-10-one in 100 ml. of dried tetrahydrofuran is added dropwise with stirring under nitrogen to a suspension of 3.1 g. of lithium aluminum hydride in 100 ml. of tetrahydrofuran. The reaction mixture is stirred for 18 hours under reflux, then cooled in an ice bath and treated under nitrogen, with stirring, with 3 ml. of water, 3 ml. of 15% sodium hydroxide and finally with 9 ml. of water. The complex is filtered and washed thoroughly with ether. The combined filtrate and washings are dried over sodium sulfate and filtered. The filtrate is concentrated to a dark blue oil. A 50 ml. portion of hexane:ether (10:1) is added and the mixture is stored in a chill room overnight. The solid is filtered, washed with hexane and dried. A second crop is obtained from the filtrate and is washed with hexane and dried. The two crops are combined, heated to solution in 100 ml. of hexane, filtered and cooled giving blue crystals which are collected, washed with hexane and dried, mp. 78°–79° C.

EXAMPLE 22

9-Allyl-4,9-dihydro-10H-thieno[3,4-b][1,5]benzodiazepin-10-one

An 11.8 g. portion of 4,9-dihydro-10H-thieno[3,4-b][1,5]benzodiazepin-10-one and 2.8 g. of 50% sodium hydride in mineral oil in 175 ml. of dimethylformamide is stirred for 2 hours. A 9 g. (6.4 ml.) portion of allyl bromide is added with stirring and the mixture is stirred overnight at room temperature. The reaction mixture is poured into ice water. The oily brown solid is collected by filtration and dissolved in methylene chloride. The filtrate is extracted twice with methylene chloride. The extracts are combined, washed with water, dried over sodium sulfate, filtered, and concentrated on a steam bath to a dark brown oily solid. The solid is swirled several times with fresh portions of hexane and then stored in a mixture of 50 ml. of hexane and 150 ml. of ether in a chill room. The crude product is collected, dissolved in 10 ml. of methylene chloride and chromatographed on an alumina column. After an initial elution with 500 ml. of hexane to remove the mineral oil, the column is eluted with 30% methylene chloride in hexane, recovering fractions 1–5 (200 ml. each), then 50% methylene chloride in hexane, recovering fractions 6-9 (200 ml. each) and finally with methylene chloride, recovering fractions 10-15 (200 ml. each). Fractions 3-9 are combined and concentrated to a red-orange viscous oil. The oil is triturated with ether, giving pale yellow crystals which are collected, washed with ether and dried (A). Fractions 10-15 are combined and concentrated to dryness giving a red-orange oil (B). Seeds of (A) are added to (B) giving pale yellow crystals of the desired product, mp. 105°-106° C.

EXAMPLE 21

9-Allyl-9,10-dihydro-4H-thieno[3,4-b][1,5]benzodiazepine

A solution of 4.6 g. of 9-allyl-4,9-dihydro-10H-thieno[3,4-b][1,5]benzodiazepin-10-one in 100 ml. of dried tetrahydrofuran is added dropwise with stirring, under nitrogen, to a suspension of 2.9 g. of lithium aluminum hydride in 100 ml. of dried tetrahydrofuran. The reaction mixture is heated under reflux with stirring overnight, then cooled in an ice bath and treated, with stirring under nitrogen, with 3 ml. of water, 3 ml. of 15% sodium hydroxide and finally with 9 ml. of water. The complex is filtered and washed several times with ether. The combined filtrate and washings are dried over sodium sulfate, filtered and the filtrate is concentrated to a dark blue oil. This oil is dissolved in 20 ml. of 30% methylene chloride in hexane and chromatographed on an alumina column as described in the previous example. Concentration of the solvent mixture yields a dark green oil which is heated to boiling in 80 ml. of hexane. The boiling hexane is decanted from a dark brown insoluble oil and then cooled giving crystals of the desired product, mp. 67°-69° C.

EXAMPLE 24

6,7-Dichloro-4,9-dihydro-9-methyl-10H-thieno[3,4-b][1,5]benzodiazepin-10-one

A reaction mixture comprising 106 g. of 4,5-dichloro-o-phenylenediamine and 96 g. of tetrahydro-4-oxo-3-thiophene carboxylic acid, methyl ester in 4 liters of benzene is refluxed for 5 hours and then cooled overnight. The benzene is removed by distillation and replaced by toluene. The mixture is refluxed 2 hours, 10 ml. of water and 0.5 ml. of acetic acid are added and the mixture is refluxed overnight, cooled to room temperature and filtered. The solid is washed with three 100 ml. portions of toluene and air dried giving 6,7-dichloro-1,3,4,9-tetrahydro-10H-thieno[3,4-b][1,5]benzodiazepin-10-one.

A 246 g. portion of the compound prepared as described above is suspended in 1.4 liters of pyridine (dried over molecular sieves) and chilled to less than 10° C. A 127 g. portion of N-chlorosuccinimide (recrystallized from benzene) is added in portions, with stirring over 2½ hours, while the temperature is maintained at 5° to 10° C. The mixture is stirred an additional 20 minutes at 5° to 10° C., warmed over a one hour period to 25° C., then warmed on a steam bath to 80° C. and held at 85°-90° C. for 40 minutes. The mixture is poured into 5 kg. of ice and allowed to stand overnight. The mixture is stirred, filtered, washed with water and dried giving 6,7-dichloro-4,9-dihydro-10H-thieno[3,4-b][1,5]benzodiazepin-10-one.

A reaction mixture comprising 13.3 g. of the latter product and 2.4 g. of 50% sodium hydride in mineral oil in 150 ml. of dry dimethylformamide is stirred at room temperature for 2 hours then 9 g. (4 ml.) of methyl iodide is added and stirring is continued at room temperature overnight. The mixture is poured onto ice and after standing for one hour, the dark brown crystalline product is collected, washed with water and dried. This solid is boiled three times in separate 250 ml. portions of methanol. The combined methanol extracts are heated to boiling, treated with charcoal and filtered through diatomaceous earth. The filtrate is concentrated to 300 ml. and placed in a chill room. The first crop of crystals is collected, washed with methanol and dried. These crystals are heated in 300 ml. of methanol and filtered, removing insoluble material (A). The filtrate is concentrated to about 100 ml. and cooled producing brown crystals which are collected, washed with ether and dried (B). (A) and (B) are combined, dissolved in 300 ml. of boiling acetone, filtered and the filtrate is concentrated to 125 ml. and placed in a chill room. The crystals which form are collected, washed with acetone and dried, giving the desired final product, mp. 265°-267° C.

EXAMPLE 25

6,7-Dichloro-9,10-dihydro-9-methyl-4H-thieno[3,4-b][1,5]benzodiazepine

To a suspension of 4 g. of lithium aluminum hydride in 150 ml. of tetrahydrofuran stirred under nitrogen, is added a solution of 10 g. of 6,7-dichloro-4,9-dihydro-9-methyl-10H-thieno[3,4-b][1,5]benzodiazepin-10-one in 350 ml. of tetrahydrofuran. The mixture is stirred under reflux for 3½ hours and then allowed to stand overnight. The mixture is cooled in an ice bath and treated, under nitrogen with stirring, with 4 ml. of water, 4 ml. of 15% sodium hydroxide and 12 ml. of water. The complex is filtered and washed with ether. The combined filtrate and washing is dried over sodium sulfate, filtered and concentrated to a residue. This residue is dissolved in a mixture of 10 ml. of 30% methylene chloride in hexane and 10 ml. of methylene chloride and chromatographed on an alumina column as described in Example 20. Those fractions which contain the desired product as determined by thin layer chromatography are combined and concentrated to give a blue-green crystalline solid. The crystalline product is heated to the boil in 200 ml. of hexane, and filtered. The filtrate is cooled and an standing produces a solid which is collected, washed with hexane and dried giving the desired product, mp. 92°-93° C.

EXAMPLE 24

6,7-Dichloro-9,10-dihydro-4H-thieno[3,4-b][1,5]benzodiazepine

A reaction mixture comprising 6.8 g. of 6,7-dichloro-4,9-dihydro-10H-thieno[3,4-b][1,5]benzodiazepin-10-one (prepared as described in Example 22) in 125 ml. of dried tetrahydrofuran and 2.9 g. of lithium aluminum hydride in 100 ml. of dried tetrahydrofuran is refluxed for 7 hours and then allowed to stand overnight. The mixture is cooled in an ice bath and treated with stirring with 3 ml. of water, 3 ml. of 15% sodium hydroxide and 9 ml. of water. The complex is filtered, washed with ether and the combined filtrate and washings are dried over sodium sulfate, filtered and evaporated under pressure on a steam bath to an oily residue. The residue is triturated in hexane. The crystals are collected, washed with hexane and dried. This crude product is purified by chromatography on an alumina column, dissolving the product in and eluting with 10% ethyl acetate in benzene. Fractions of 50 ml. are collected. Fractions 2-4 are combined and concentrated to crystals. These crystals are dissolved with heating in 30 ml. of benzene, filtered and the filtrate placed in a cold room. The resulting crystals are collected washed with hexane and dried giving the desired product, mp. 195°-197° C.

EXAMPLE 27

4,9-Dihydro-4-propionyl-10H-thieno[3,4-b][1,5]benzodiazepin-10-one

A reaction mixture comprising 9.9 g. of 4,9-dihydro-10H-thieno[3,4-b][1,5]benzodiazepin-10-one and 4.7 g. (4.4 ml.) of propionyl chloride in 100 ml. of benzene is refluxed for 3 hours and allowed to stand overnight. The precipitate is collected, washed with benzene and dried. A 3 g. portion of this solid is heated to boiling in 125 ml. of ethyl acetate, filtered and the filtrate is cooled. The solid is collected, washed with hexane and dried giving the desired product, mp. 222°-224° C.

EXAMPLE 28

9,10-Dihydro-4-n-propyl-4H-thieno[3,4-b][1,5]benzodiazepine hydrochloride

To a suspension of 5.8 g. of lithium aluminum hydride in 150 ml. of dried tetrahydrofuran under nitrogen is added, with stirring, a solution of 4.6 g. of 4,9-dihydro-4-propionyl-10H-thieno[3,4-b][1,5]benzodiazepin-10-one in 150 ml. of tetrahydrofuran. The mixture is refluxed for 20 hours with stirring, then cooled and 6 ml. of water, 6 ml. of 15% sodium hydroxide and 18 ml. of water are added dropwise, under nitrogen. The complex is filtered and washed with ether. The combined filtrate and washings are dried over sodium sulfate, filtered and evaporated to a residue. The residue is triturated in ether:hexane (50:50). The first crop is removed by filtration. The filtrate is chilled and a second crop is filtered off. The filtrate is concentrated to an oil. The oil is treated with 5 ml. of 3N ethanolic hydrochloric acid and 20 ml. of ether is added. The solid is collected, washed with ether and dried. This solid is heated to solution in 250 ml. of acetone, filtered and the filtrate is concentrated to 125 ml. A 125 ml. portion of ether is added, the mixture is cooled for 4 hours and the solid is collected, washed with ether and dried giving the desired product, mp. 190°-192° C.

EXAMPLE 29

4,9-Dihydro-9-methyl-4-propionyl-10H-thieno[3,4-b][1,5]benzodiazepin-10-one

A reaction mixture comprising 7 g. of 4,9-dihydro-9-methyl-10H-thieno[3,4-b][1,5]benzodiazepin-10-one, 3.1 g. (2.9 ml.) of propionyl chloride and 70 ml. of benzene is refluxed for 3 hours and then allowed to stand for 48 hours. The benzene is distilled off. The residue is filtered, washed with ether and dried. The solid is heated to boiling in 300 ml. of ethyl acetate, filtered and the filtrate is chilled. The crystals are collected, washed with ether and dried giving the desired product, mp. 202°-203° C.

EXAMPLE 30

9,10-Dihydro-9-methyl-4-propyl-4H-thieno[3,4-b][1,5]benzodiazepine

A 5 g. portion of 4,9-dihydro-9-methyl-4-propionyl-10H-thieno[3,4-b][1,5]benzodiazepin-10-one is added to 200 ml. of tetrahydrofuran. To this is added 140 ml. of 1M borane, over a 15 minute period in an ice bath under nitrogen. The mixture is refluxed for 20 hours, then cooled in an ice bath and 40 ml. of 6N hydrochloric acid is added dropwise, with stirring. The tetrahydrofuran is distilled off. The reaction mixture is stirred with ice bath cooling and 31 g. of sodium hydroxide pellets are carefully added portionwise. The mixture is extracted twice with 250 ml. of benzene. Water is added to solubilize some salts. The mixture is extracted with 250 ml. of ether. The ether and benzene extracts are combined, dried over sodium sulfate, filtered and concentrated to an oil. This oil is treated with 75 ml. of ether:hexane (50:50), cooled and filtered. The filtrate is diluted with 50 ml. of hexane and cooled for a prolonged period. The solvent mixture is decanted from the insoluble material and concentrated to a solid residue. The residue is dissolved in 60 ml. of 10% methylene chloride in hexane and chromatographed on an alumina column. The column is eluted with 10% methylene chloride in hexane, discarding the first 500 ml. of eluant. Fractions 2 and 3 are collected (200 ml. each) and the eluate is changed to 20% methylene chloride in hexane. Fractions 2-7 (200 ml. each) are combined and concentrated giving the desired product as pale yellow crystals, mp. 90°-92° C.

EXAMPLE 31

4,9-Dihydro-4-hexanoyl-10H-thieno[3,4-b][1,5]benzodiazepin-10-one

A 9 g. portion of 4,9-dihydro-10H-thieno[3,4-b][1,5]benzodiazepin-10-one and 6.3 g. (6.6 ml.) of hexanoyl chloride in 100 ml. of benzene is refluxed for 3 hours. The benzene is distilled off. The residue is triturated in ether, washed with ether and dried. This solid is heated to boiling in 250 ml. of benzene, filtered and the filtrate is diluted with 250 ml. of hexane. This mixture is filtered and then cooled. The solid is collected, washed with hexane and dried giving the desired product, mp. 127°-129° C.

EXAMPLE 32

4,9-Dihydro-4-hexyl-10H-thieno[3,4-b][1,5]benzodiazepin-10-one and
9,10-dihydro-4-hexyl-4H-thieno[3,4-b][1,5]benzodiazepine hydrochloride To a suspension of 5.4 g. of lithium aluminum hydride in 150 ml. of tetrahydrofuran under nitrogen, with stirring, is added 5 g. of 4,9-dihydro-4-hexanoyl-10H-thieno[3,4-b][1,5]benzodiazepin-10-one in 100 ml. of tetrahydrofuran. The reaction mixture is stirred under reflux overnight. The mixture is cooled and there is added carefully, under nitrogen, 5.4 ml. of water, 5.4 ml. of 15% sodium hydroxide and then 16 ml. of water. The complex is filtered and washed with ether. The combined filtrate and washing is dried over sodium sulfate filtered and concentrated to an oil. The oil is boiled in 100 ml. of hexane. The hexane is decanted and concentrated to an oil. This oil is dissolved with warming in 10 ml. of 20% methylene chloride in hexane and chromatographed on an alumina column, eluting with the same solvent mixture. The first 75 ml. of eluate is discarded. Fractions 1-7 (50 ml.) are collected. The eluate is changed to 40% methylene chloride in hexane and fractions 8-15 (50 ml.) are collected. The eluate is changed to 60% methylene chloride in hexane and fractions 16-18 (50 ml.) and fractions 19-30 (100 ml.) are collected. The eluate is changed to methylene chloride and fractions 31-33 (100 ml.) are collected. The eluate is changed to 20% methanol in methylene chloride and fractions 34–37 (100 ml.) are collected.

Fractions 1–13 are combined and concentrated giving a green oil. This oil is dissolved in 50 ml. of ether, acidified with 5 ml. of 3N ethanolic hydrochloric acid and concentrated to dryness. A 5 ml. portion of 3N ethanolic hydrochloric acid and excess ether are added producing crystals which are collected, washed with ether and dried. These crystals are dissolved with warming in 10 ml. of ethanol, diluted with 40 ml. of ether and cooled. The crystals are collected, washed with ether and dried giving the product 9,10-dihydro-4-hexyl-4H-thieno[3,4-b][1,5]benzodiazepine hydrochloride, mp. 143°–145° C.

Fractions 31–35 are combined and concentrated to a dark green oil. Hexane is added and the mixture is chilled overnight. The crystals are collected, washed with hexane and dried giving the product 4,9-dihydro-4-hexyl-10H-thieno[3,4-b][1,5]benzodiazepin-10-one, mp. 112°–113° C.

EXAMPLE 33

4,9-Dihydro-9-(2-methylallyl)-10H-thieno[3,4-b][1,5]benzodiazepin-10-one

An 11.8 g. portion of 4,9-dihydro-10H-thieno[3,4-b][1,5]benzodiazepin-10-one in 175 ml. of dimethylformamide is stirred. A 2.8 g. portion of 50% sodium hydride in mineral oil is treated with hexane to remove the mineral oil and then added to the reaction mixture. After 2 hours of stirring, 6.7 g. (7.2 ml.) of methallyl chloride is added. The mixture is stirred overnight and poured into ice-water. The mixture is extracted with four 250 ml. portions of methylene chloride. The extracts are combined, washed with water, dried over sodium sulfate, filtered and concentrated to dryness. The crude product is dissolved in 10 ml. of 40% methylene chloride in hexane and chromatographed on an alumina column, eluting with the same solvent. Those fractions which contain the desired product as determined by thin layer chromatography are combined and concentrated to give the crude product. This product is heated to solution in 25 ml. of benzene, filtered and the solid which forms is collected, washed with hexane and dried giving the desired product, mp. 161°–163° C.

EXAMPLE 34

9,10-Dihydro-9-(2-methylallyl)-4H-thieno[3,4-b][1,5]benzodiazepine

A 4.9 g. portion of 4,9-dihydro-9-(2-methylallyl)-10H-thieno[3,4-b][1,5]benzodiazepin-10-one in 100 ml. of dried tetrahydrofuran is added with stirring and ice bath cooling, under nitrogen, to 2.9 g. of lithium aluminum hydride in 100 ml. of dried tetrahydrofuran. The mixture is refluxed overnight and then decomposed with stirring and cooling under nitrogen by the successive addition of 3 ml. of water, 3 ml. of 15% sodium hydroxide and 9 ml. of water. The complex is filtered and washed with ether. The combined filtrate and washing is dried over sodium sulfate, filtered and evaporated to a residue on a steam bath. The residue is recrystallized from hexane giving the desired product, mp. 83°–84° C.

EXAMPLE 35

4,9-Dihydro-4-hexanoyl-9-methyl-10H-thieno[3,4-b][1,5]benzodiazepin-10-one

A mixture of 7 g. of 4,9-dihydro-9-methyl-10H-thieno[3,4-b][1,5]benzodiazepin-10-one and 4.6 g. (4.8 ml.) of hexanoyl chloride in 70 ml. of benzene is heated with stirring under reflux for 3 hours. The reaction mixture is stirred with cooling in an ice bath for 2 hours, 150 ml. of hexane is added and the mixture is placed in a chill room. The solvents are removed in vacuo on a steam bath. A 10 ml. portion of ether is added to the residue and the mixture is returned to the chill room. The tan crystals are collected by filtration, washed with ether and dried. The ether is concentrated giving a green oil which is triturated twice with hexane and once with a mixture of hexane and ether, giving crystals which are collected, washed with ether and dried. The two crops of crystals are combined, dissolved with warming in 75 ml. of ether and filtered. The filtrate is concentrated to 35 ml. and stored in a cold room for 4 hours. The solid is collected, washed with ether then hexane and dried, giving the desired product, mp. 76°–77° C.

EXAMPLE 36

9,10-Dihydro-4-n-hexyl-9-methyl-4H-thieno[3,4-b][1,5]benzodiazepine

To a reaction mixture comprising 3.6 g. of 4,9-dihydro-4-hexanoyl-9-methyl-10H-thieno[3,4-b][1,5]benzodiazepin-10-one in 100 ml. of tetrahydrofuran is added, over a 15 minute period, with stirring, in an ice bath, under nitrogen, 90 ml. of 1M-borane. The reaction mixture is then refluxed with stirring for 19 hours. The mixture is cooled in an ice bath and 30 ml. of 6N hydrochloric acid is added dropwise with stirring. The tetrahydrofuran is removed by distillation and 23 g. of sodium hydroxide pellets are carefully added in the cold with stirring. A 15 ml. portion of water is added and the mixture is extracted with three 150 ml. portions of benzene. The benzene extracts are combined, washed with water, dried over sodium sulfate, filtered and concentrated to an oil. This crude product is dissolved in 10 ml. of 20% methylene chloride in hexane and chromatographed on an alumina column, eluting with the same solvent system. The first 150 ml. of eluent is discarded, then 100 ml. fractions are collected. Fractions 1–5 are combined and concentrated to an oil. The oil is extracted with ether repeatedly. The ether extracts are combined, washed with water, dried over sodium sulfate, filtered and concentrated to a residue. The residue is dissolved in 10 ml. of ether and shaken with 25 ml. of 1N sodium hydroxide. The ether is washed with water, dried over sodium sulfate, filtered and concentrated to residue. This residue is dissolved in 25 ml. of methylene chloride and purified by chromatography on a magnesol column, eluting with methylene chloride. The eluant is concentrated giving the desired product as a dark amber oil.

EXAMPLE 37

4,9-Dihydro-6-nitro-10H-thieno[3,4-b][1,5]benzodiazepin-10-one

A reaction mixture comprising 91.8 g. of 4-nitro-o-phenylenediamine and 96 g. of tetrahydro-4-oxo-3-thiophene carboxylic acid, methyl ester in 3.2 liters of toluene is refluxed for 2½ hours, 600 ml. of methanol is added and refluxing is continued overnight. The methanol is distilled off, 500 ml. of toluene is added and refluxing is continued for 48 hours. The mixture is filtered. The crystals are washed with one liter of benzene, boiled with 2 liters of methanol and filtered. The crystals are slurried with 2 liters of hot methanol and dried, giving 134.0 g. of 6-nitro-1,3,4,9-tetrahydro-10H-thieno[3,4-b][1,5]benzodiazepin-10-one as red crystals.

A 28.6 g. portion of N-chlorosuccinimide is added over a 30 minute period to a slurry of 131.5 g. of the above intermediate in 2 liters of pyridine at 3° C. The mixture is stirred and slowly warmed to room temperature, then heated on a steam bath for 30 minutes. The solid is filtered and washed with pyridine and hexane. The filtrate is allowed to stand for a prolonged period. The crystals which form are collected and washed with methanol. These crystals are dissolved in 250 ml. of hot dimethylformamide, filtered and the filtrate is diluted with 200 ml. of absolute ethanol giving the desired product as orange crystals.

EXAMPLE 38

9,10-Dihydro-6-nitro-4H-thieno[3,4-b][1,5]benzodiazepine

An 8 g. portion of 4,9-dihydro-6-nitro-10H-thieno[3,4-b][1,5]benzodiazepin-10-one in 155 ml. of tetrahydrofuran is stirred, under nitrogen, with cooling in an ice bath. To this is added slowly with stirring 155 ml. of 1M borane in tetrahydrofuran over a period of 15 minutes. The reaction mixture is then stirred at room temperature for one hour and then heated under reflux with stirring for 5 hours. The mixture is stirred at room temperature for 48 hours. The mixture is stirred and cooled in an ice bath while 45 ml. of 6N hydrochloric acid is added dropwise. The tetrahydrofuran is distilled off on a steam bath and the acidic residue is treated portionwise, with swirling in ice with 35 g. of sodium hydroxide pellets. The reaction mixture is extracted with benzene. The benzene extracts are concentrated, and the residue is repeatedly triturated with ether and filtered. The ether filtrate produces red crystals which are collected, washed with ether and dried. This solid is heated in 60 ml. of benzene to solution, filtered, and the filtrate is concentrated to 30 ml. and cooled. The solid is collected, washed with benzene and hexane and dried giving the desired product, mp. 184°–186° C.

EXAMPLE 39

4-Acetyl-4,9-dihydro-9-methyl-10H-thieno[3,4-b][1,5]benzodiazepin-10-one

A mixture of 7 g. of 4,9-dihydro-9-methyl-10H-thieno[3,4-b][1,5]benzodiazepin-10-one and 2.7 g. of acetyl chloride in 75 ml. of benzene is heated under reflux with stirring for 3 hours. The reaction mixture is cooled in an ice bath and two crops of brown crystals are collected, washed with benzene, dried and combined. Concentration of the benzene provides a third crop which is combined with the first two crops, heated to boiling in 250 ml. of ethyl acetate and filtered while hot. An equal amount of hexane is added, the mixture is cooled and the solid is collected, washed with hexane and dried, giving the desired product, mp. 197°–199° C.

EXAMPLE 40

9,10-Dihydro-4-ethyl-9-methyl-4H-thieno[3,4-b][1,5]benzodiazepine

A 150 ml. portion of 1M-borane in tetrahydrofuran is added with stirring and cooling to a solution of 5.1 g. of 4-acetyl-4,9-dihydro-9-methyl-10H-thieno[3,4-b][1,5]-benzodiazepin-10-one in 200 ml. of tetrahydrofuran. The reaction mixture is heated under reflux for 20 hours, cooled in an ice bath and 52 ml. of 6N hydrochloric acid is added dropwise with stirring. The tetrahydrofuran is removed by distillation. A 40 g. portion of sodium hydroxide pellets is carefully added in the cold with stirring followed by 25 ml. of water. The mixture is extracted with three 150 ml. portions of benzene. The benzene extracts are combined, washed with water, dried over sodium sulfate, filtered and concentrated to dryness. The residue is extracted three times with boiling hexane. The combined hexane extracts are cooled and the solid is collected, washed with hexane and ether and dried. A second crop is recovered from the hexane filtrate and combined with the first crop. The solid is dissolved in 25 ml. of methylene chloride, filtered and the solvent is evaporated almost to dryness. A 50 ml. portion of hexane is added. The solid is collected, washed with hexane and dried, giving the desired product as white crystals, mp. 135°–137° C.

EXAMPLE 41

4,9-Dihydro-4,9-dimethyl-10H-thieno[3,4-b][1,5]benzodiazepin-10-one

A mixture of 2.8 g. of 4,9-dihydro-4-methyl-10H-thieno[3,4-b][1,5]benzodiazepin-10-one and 620 mg. of 50% sodium hydride in mineral oil in 30 ml. of dry dimethylformamide is stirred for 1¼ hours. A 2.1 g. portion of methyl iodide is added and the mixture is stirred overnight. The mixture is poured onto ice water and the solid is collected and dried. The solid changes to a glass which is dissolved in methylene chloride, washed with water, filtered and concentrated to dryness. The crude oily solid is triturated in hexane and ether. The ether hexane mixture is concentrated to a yellow gum, dissolved in 15 ml. of 30% methylene chloride in hexane and chromatographed on an alumina column, eluting with the same solvent. Four 200 ml. fractions are collected. The solvent is changed to methylene chloride:hexane (50:50) for fractions 5–8 (200 ml.). The solvent is changed to 100% methylene chloride for fractions 8–11 (200 ml.). The solvent is changed to 20% ethyl acetate in benzene for fractions 12–19 (200 ml.). Fractions 11–19 are combined and concentrated to a yellow oil which crystallizes with trituration in hexane, giving the desired product, mp. 101°–102° C.

EXAMPLE 42

4,9-Dihydro-9-phenethyl-10H-thieno[3,4-b][1,5]benzodiazepin-10-one

To a solution of 17.28 g. of 4,9-dihydro-10H-thieno[3,4-b][1,5]benzodiazepin-10-one in 100 ml. of dimethylformamide is added 4.2 g. of 50% sodium hydride in mineral oil. The mixture is stirred for one hour and 16.0 g. of phenethyl bromide and 20 mg. of potassium iodide are added. The mixture is stirred for 48 hours. The solution is evaporated. The residual gum is washed with water and hexane, dissolved in methylene chloride, washed with water, dried over magnesium sulfate and filtered through magnesol. The crystals which form in the filtrate are removed by filtration. This filtrate is evaporated in vacuo giving the desired product as dark brown crystals.

EXAMPLE 43

9-[4-chloro-3-(trifluoromethyl)benzyl]-4,9-dihydro-10H-thieno[3,4-b][1,5]benzodiazepin-10-one To a solution of 8.64 g. of 4,9-dihydro-10H-thieno[3,4-b][1,5]benzodiazepin-10-one in 100 ml. of dimethylformamide is added 2.1 g. of 50% sodium hydride in mineral oil. The mixture is stirred for one hour and 10.0 g. of 4-chloro-3-trifluoromethyl benzyl chloride and 10 mg of potassium iodide are added. The mixture is stirred for a prolonged period and the solvent is removed in vacuo. The residual gum is dissolved in methylene chloride, dried over magnesium sulfate and filtered through magnesol. The filtrate is evaporated to give tan crystals which are recrystallized from ethanol giving the desired product as off-white crystals, mp. 181°–183° C.

EXAMPLE 44

9-(2-Cyclohexen-1-yl)-4,9-dihydro-10H-thieno[3,4-b][1,5]benzodiazepin-10-one

To a mixture of 11.8 g. of 4,9-dihydro-10H-thieno[3,4-b][1,5]benzodiazepin-10-one in 175 ml. of dimethylformamide is added 2.8 g. of 50% sodium hydride in mineral oil from which the mineral oil has been removed. The mixture is stirred for two hours and then 11.9 g. of 3-bromocyclohexene is added. The reaction mixture is stirred overnight and poured into ice water. The brown syrup which separates is collected and extracted into methylene chloride. The extracts are washed with water, dried over sodium sulfate, filtered and evaporated to an oil. The oil is triturated in ether-hexane and cooled for 48 hours. The mixture is separated by partition chromatography. Fraction 3 is triturated in hexane, filtered and the solid is dried. The solid is triturated in hexane and chilled producing crystals. The crystals are collected, washed with hexane and dried. These crystals are heated to solution in 12 ml. of ethanol and cooled. A 12 ml. portion of hexane is added and the tan crystals are collected, washed with hexane and dried giving the desired product, mp. 147°–149° C.

EXAMPLE 45

4-Acetyl-9,10-dihydro-9-ethyl-10H-thieno[3,4-b][1,5]benzodiazepin-10-one

A mixture of 14 g. of 4,9-dihydro-9-ethyl-10H-thieno[3,4-b][1,5]benzodiazepin-10-one and 5 g. of acetyl chloride in 150 ml. of benzene is heated with stirring under reflux for 3 hours and then allowed to stand at room temperature overnight. The mixture is concentrated to 75 ml., cooled for 2 hours and 50 ml. of hexane is added. The mixture is placed in a chill room. The solid is collected, washed with hexane, dried, dissolved in 75 ml. of hot benzene, filtered and allowed to stand at room temperature. The solid is collected, washed with benzene and then hexane and dried, giving the desired product, mp. 88°–90° C.

We claim:

1. A compound selected from the group consisting of those of the formula:

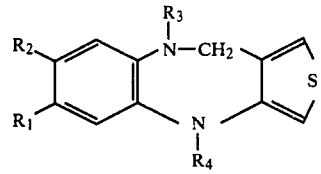

wherein $R_1$ and $R_2$ are each individually selected from the group consisting of hydrogen, chloro, hydroxy, methoxy, trifluoromethyl, nitro, amino and alkyl having up to 4 carbon atoms; $R_3$ is selected from the group consisting of hydrogen, alkyl having up to 6 carbon atoms and alkenyl having from 3 to 6 carbon atoms; and $R_4$ is selected from the group consisting of hydrogen, alkyl having up to 6 carbon atoms, cycloalkylmethyl having from 4 to 7 carbon atoms, benzyl and β-phenethyl; and the pharmacologically acceptable acid-addition and quaternary ammonium salts thereof.

2. The compound according to claim 1 wherein $R_1$, $R_2$, $R_3$ and $R_4$ are all hydrogen; 9,10-dihydro-4H-thieno[3,4-b][1,5]benzodiazepine.

3. The compound according to claim 1 wherein $R_1$, $R_2$ and $R_4$ are all hydrogen and $R_3$ is methyl; 9,10-dihydro-9-methyl-4H-thieno[3,4-b][1,5]benzodiazepine.

4. The compound according to claim 1 wherein $R_1$, 2 and $R_3$ are all hydrogen and $R_4$ is methyl; 9,10-dihydro-4-methyl-4H-thieno[3,4-b][1,5]benzodiazepine.

5. The compound according to claim 1 wherein $R_1$, $R_2$ and $R_4$ are all hydrogen and $R_3$ is ethyl; 9,10-dihydro-9-ethyl-4H-thieno[3,4-b][1,5]benzodiazepine.

6. The compound according to claim 1 wherein $R_1$, $R_2$ and $R_3$ are all hydrogen and $R_4$ is ethyl; 9,10-dihydro-4-ethyl-4H-thieno[3,4-b][1,5]benzodiazepine.

7. The compound according to claim 1 wherein $R_1$ and $R_2$ are chloro, $R_3$ is methyl and $R_4$ is hydrogen; 6,7-dichloro-9,10-dihydro-9-methyl-4H-thieno[3,4-b][1,5]benzodiazepine.

8. The compound according to claim 1 wherein $R_1$ and $R_2$ are hydrogen, $R_3$ is methyl and $R_4$ is ethyl; 9,10-dihydro-4-ethyl-9-methyl-4H-thieno[3,4-b][1,5]benzodiazepine.

9. The compound according to claim 1 wherein $R_1$, $R_2$ and $R_4$ are all hydrogen and $R_3$ is allyl; 9-allyl-9,10-dihydro-4H-thieno[3,4-b][1,5]benzodiazepine.

10. The compound according to claim 1 wherein $R_1$, $R_2$ and $R_4$ are all hydrogen and $R_3$ is n-propyl; 9,10-dihydro-9-n-propyl-4H-thieno[3,4-b][1,5]benzodiazepine.

* * * * *